United States Patent
Murphy

(10) Patent No.: US 10,117,497 B1
(45) Date of Patent: Nov. 6, 2018

(54) LIQUID DERMATOLOGICAL AGENT DISPENSING DEVICE

(71) Applicant: RLM Group Ltd., Mt. Kisco, NY (US)

(72) Inventor: Robert L. Murphy, Mt. Kisco, NY (US)

(73) Assignee: RLM Group Ltd., Mt. Kisco, NY (US)

( * ) Notice: Subject to any disclaimer, the term of this patent is extended or adjusted under 35 U.S.C. 154(b) by 0 days.

(21) Appl. No.: 15/815,041

(22) Filed: Nov. 16, 2017

(51) Int. Cl.
| | | |
|---|---|---|
| *A45D 40/24* | (2006.01) | |
| *B65D 47/42* | (2006.01) | |
| *A61F 13/40* | (2006.01) | |
| *A45D 40/00* | (2006.01) | |
| *B65D 25/52* | (2006.01) | |

(52) U.S. Cl.
CPC ......... *A45D 40/24* (2013.01); *A45D 40/0068* (2013.01); *A61M 35/006* (2013.01); *B65D 25/52* (2013.01); *B65D 47/42* (2013.01)

(58) Field of Classification Search
CPC combination set(s) only.
See application file for complete search history.

(56) References Cited

U.S. PATENT DOCUMENTS

| | | | | |
|---|---|---|---|---|
| 4,446,965 | A * | 5/1984 | Montiel | A45D 29/007 132/73 |
| 4,932,802 | A * | 6/1990 | Cantone | A45D 29/007 401/126 |
| 5,914,116 | A | 6/1999 | Suares et al. | |
| 6,457,891 | B1 | 10/2002 | Bredacts | |
| 6,491,041 | B1 * | 12/2002 | Okamoto | A45D 29/007 132/294 |
| 6,497,527 | B2 | 12/2002 | Kaufmann | |
| 7,226,227 | B2 | 6/2007 | Gueret | |
| 7,686,528 | B2 | 3/2010 | Gueret | |
| 7,743,775 | B2 * | 6/2010 | Thiebaut | A45D 40/24 132/287 |
| 7,845,871 | B2 | 12/2010 | Thiebaut | |
| 8,123,426 | B2 | 2/2012 | Byun | |
| 2004/0190974 | A1 | 9/2004 | Cantone et al. | |
| 2004/0234321 | A1 | 11/2004 | Breidenbach et al. | |
| 2011/0210039 | A1 | 9/2011 | Alongi et al. | |

\* cited by examiner

Primary Examiner — David Walczak
(74) Attorney, Agent, or Firm — K&L Gates LLP

(57) ABSTRACT

A dispensing device includes a container defining a reservoir containing a liquid and a porous applicator for dispensing the liquid. Another dispensing device includes two containers attached to each other, where the first container defines a reservoir containing a first liquid and a porous applicator for dispensing liquid and the second container contains a second liquid that may be dispensed via application of a force.

21 Claims, 20 Drawing Sheets

LIQUID DERMATOLOGICAL AGENT DISPENSING DEVICE

BACKGROUND

Figure 1A:
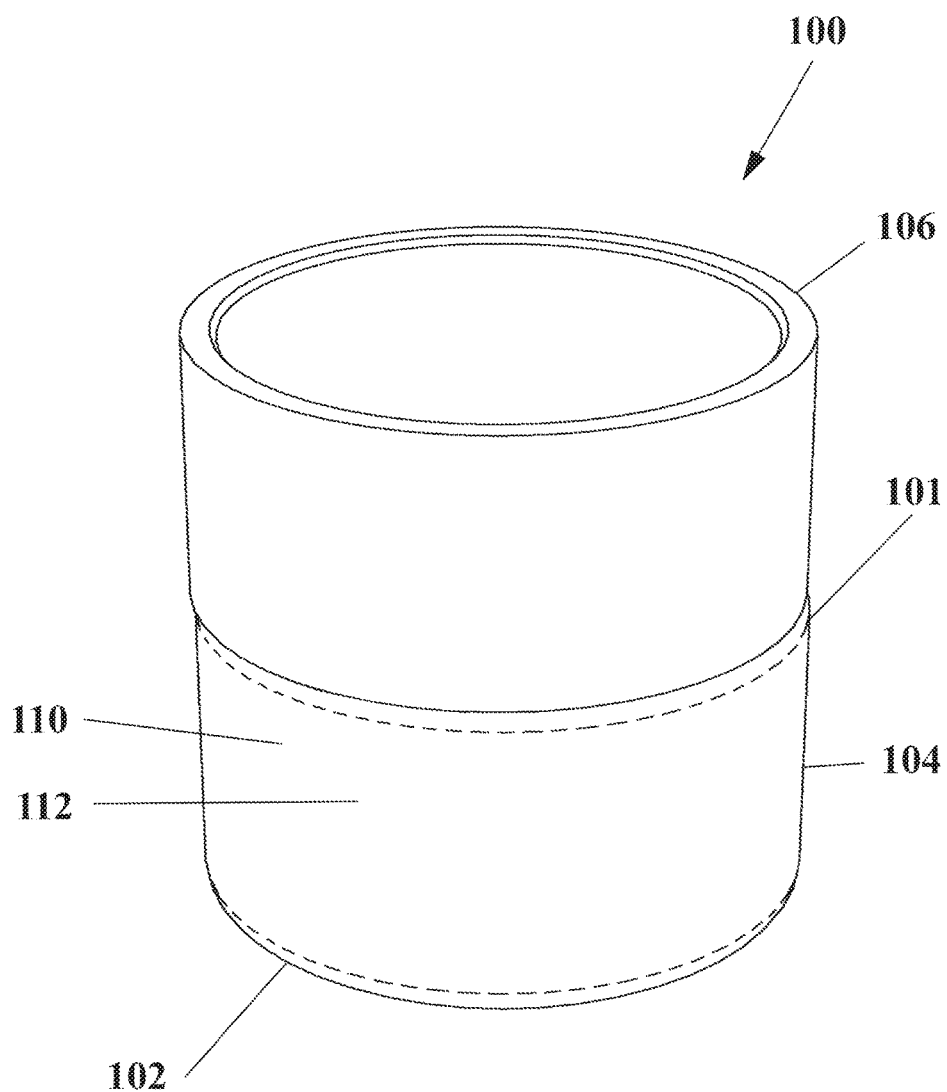

Liquid dermatological agents, such as cosmetic or pharmaceutical creams, oils or serums, can be applied with many different types of delivery means, such as aerosol sprays, roll-ons, and pumps (which are also sometimes referred to as feeder systems); or a user could simply put their finger into the liquid to apply it. Some liquid dermatological agent dispensing devices, particularly ones with low-viscosity oil, serum, liquid dermatological agents, are prone to leakage, migrating or spilling, however.

SUMMARY

In one general aspect, the present invention is directed to a dispensing device that comprises a first container having a sidewall that defines a reservoir. The first container has an upper opening to the reservoir at a top of the first container. A first liquid, that comprises a dermatological agent, is in the reservoir, along with a porous applicator. The porous applicator comprises open-celled pores that extend from a bottom of the porous applicator to a top surface of the porous applicator, such that the open-celled pores are filled with the first liquid such that the pores deliver the first liquid to the top surface of the porous applicator by capillary action, and such that the porous applicator substantially fills the reservoir and the upper opening at the top of the first container such that the first liquid is prevented from free-flowing out of the reservoir. As such, the porous applicator can deliver the first liquid to the top surface of the porous applicator without use of a pump or buffer. Additionally, as such, the porous applicator may advantageously reduce or prevent migration of low viscosity liquids such as oils or serums.

In other embodiments, the dispensing device comprises a second container, e.g., a squeeze tube, containing a second liquid that may comprise a second dermatological agent that is different from the first liquid. The second container may have a circular, threaded post at an upper end of the second container; and the first container may comprise a circular post that extends upward from a lower, central portion of the first container into the reservoir. The circular post of the first container may comprise a downward-facing threaded recess for receiving the threaded post of the second container such that first container is detachably removable from the second container by unscrewing the first container.

In various implementations, the circular post of the first container comprises an upper wall that blocks the second liquid from entering the reservoir defined by the first container. In other embodiments, the threaded post of the second container comprises a tip that extends from the threaded post of the second container into the porous applicator when the first container is attached to the second container. In such embodiments, the tip can comprise an opening for dispensing the second liquid that is in the second container. The upper (or distal) end of the tip can terminate below or at the top surface of the porous applicator when the threaded post of the second container is fully threaded into the circular post of the first container. Also, the cap can comprise a downward facing pintle that is inserted into the opening of the tip of the second container when the cap is attached to the first container and the threaded post of the second container is fully threaded into the circular post of the first container.

The dermatological agents of the first and second liquids can be cosmetic or pharmaceutical dermatological agents, such as cosmetic or pharmaceutical creams, oils, lotions, etc.

These and other benefits and features of the present invention will be apparent from the description below.

FIGURES

Figure 11:
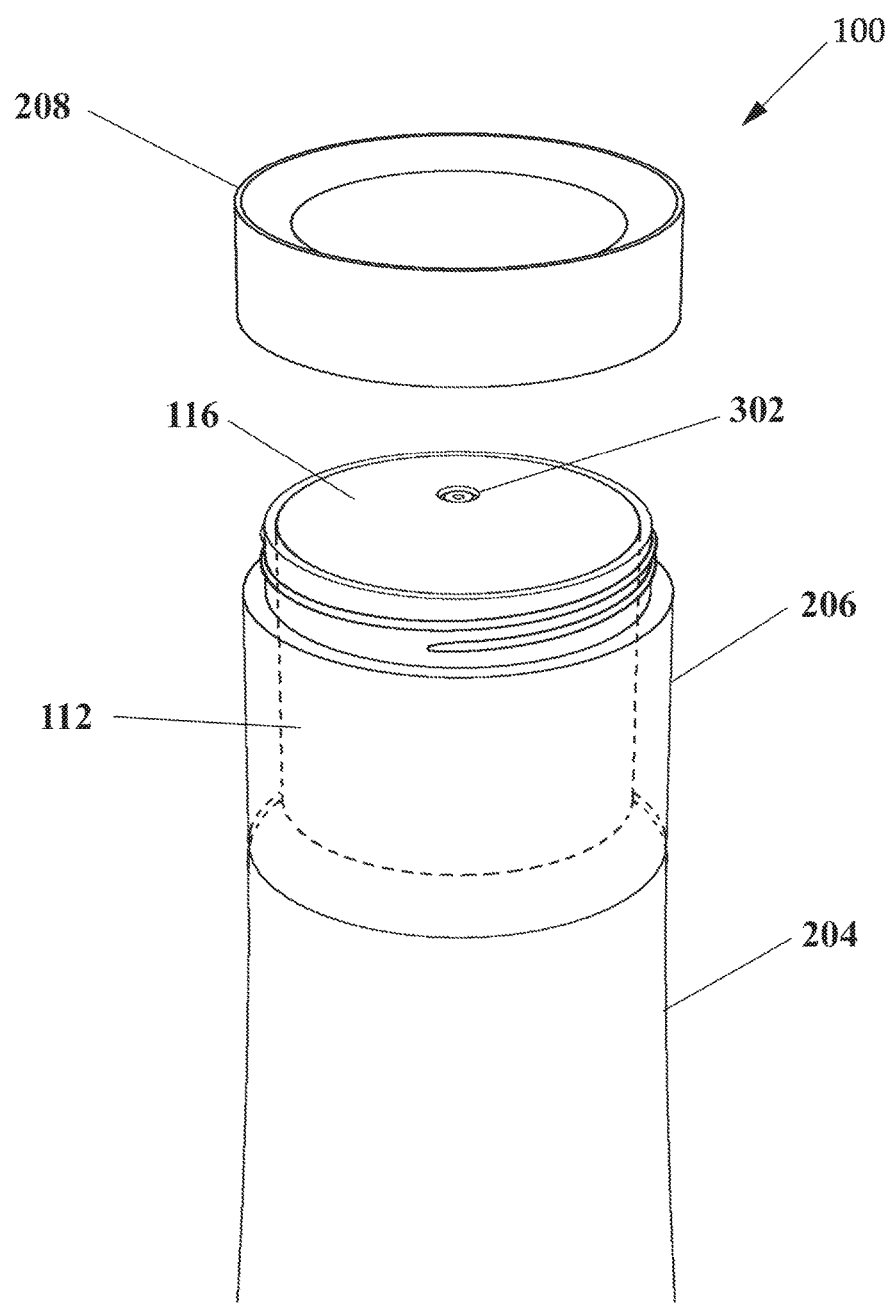
Figure 12:
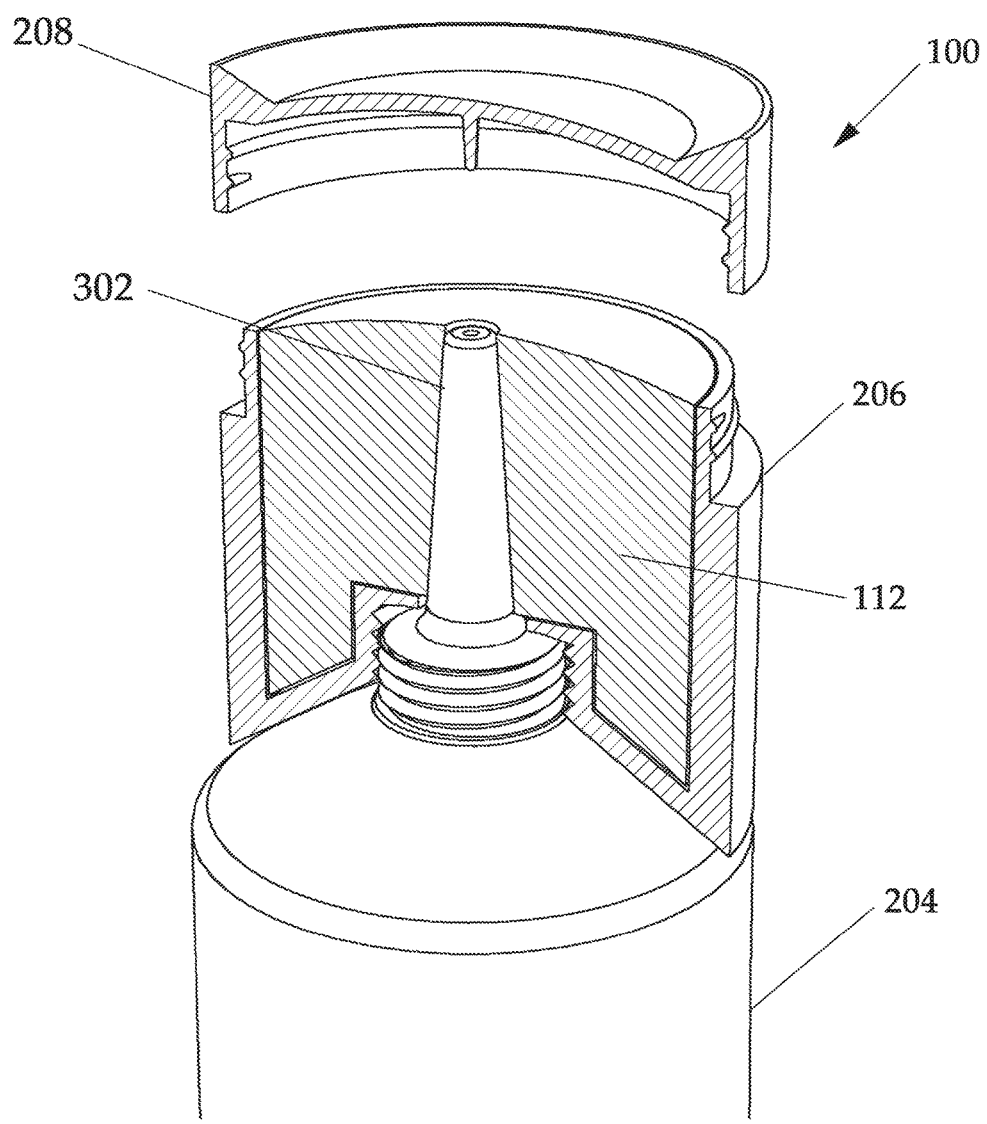

Various embodiments of the present invention are described herein by way of example in connection with the following figures, wherein:

FIGS. 1A-1C and 2 illustrate an example dispensing device that includes a porous applicator according to various embodiments of the present invention;

FIGS. 3, 4, 5A-5B, 6, and 7A-7C are views of an example dispensing device in a dual container configuration according to various embodiments of the present invention;

FIGS. 8A-8B, 9A-B, and 10A-10B are views of an example dispensing device in a dual container configuration according to other various embodiments of the present invention;

FIGS. 11 and 12 are views of an example dispensing device in a dual container configuration according to still other various embodiments of the present invention.

DESCRIPTION

In one general aspect, the present invention is directed to a dispensing device that dispenses fluids, particularly dermatological agents, such as cosmetic or pharmaceutical liquids or serums via a porous applicator. The porous applicator preferably prevents the liquid within the dispensing device from free flowing (e.g. spilling) out of the device. In various embodiments, the porous applicator delivers the liquid to the top surface of the porous applicator via capillary action. That is, for example, the porous applicator, which can form a pad or dome for easy application of the dermatological agent, wicks the liquid in the container to the top surface of the porous applicator. A user can apply the porous applicator directly to the desired skin area to dispense the liquid to the desired skin area; or the user could collect a desired amount of the liquid from the porous application on a finger or tool, and then apply the liquid to the desired skin area with the finger or tool, for example. As liquid is dispensed via the porous applicator, additional liquid of the dispensing device wicks upwards to the top surface to replenish the top surface of the porous applicator. One advantage of the dispensing device is that it facilitates the controlled application of the liquid dermatological agent while reducing or even preventing leaking or spilling. Another advantage is that dispensing device does not require a pump or buffer to deliver the liquid dermatological agent, thereby simplifying the manufacturer and operation of the dispensing device. In other words, the dispensing device does not require, and preferably does not include, a separate buffer or sealing layer for protecting against leakage that could be caused by displacement of the dispensing device. That is, for example, if a user of the dispensing device displaces the dispensing device to a 90 degree angle via accidental contact, the self-sealing porous applicator will prevent liquid dermatological agent from leaking past the top surface.

Figure 1B:
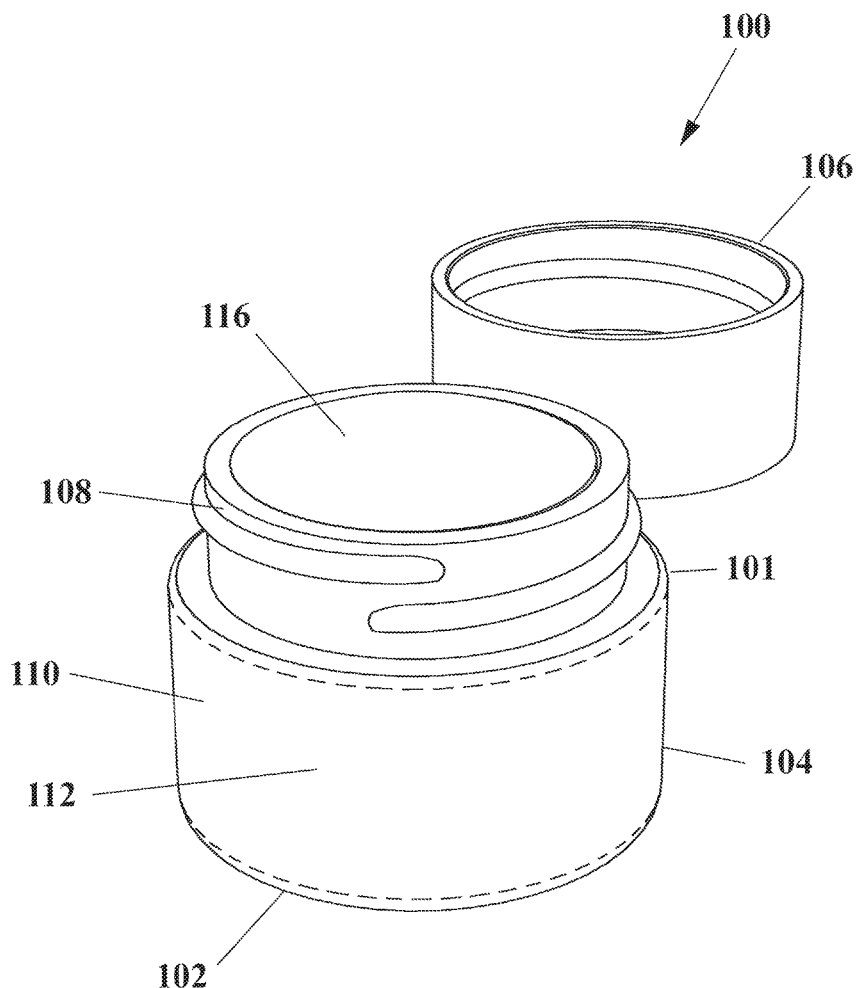
Figure 1C:
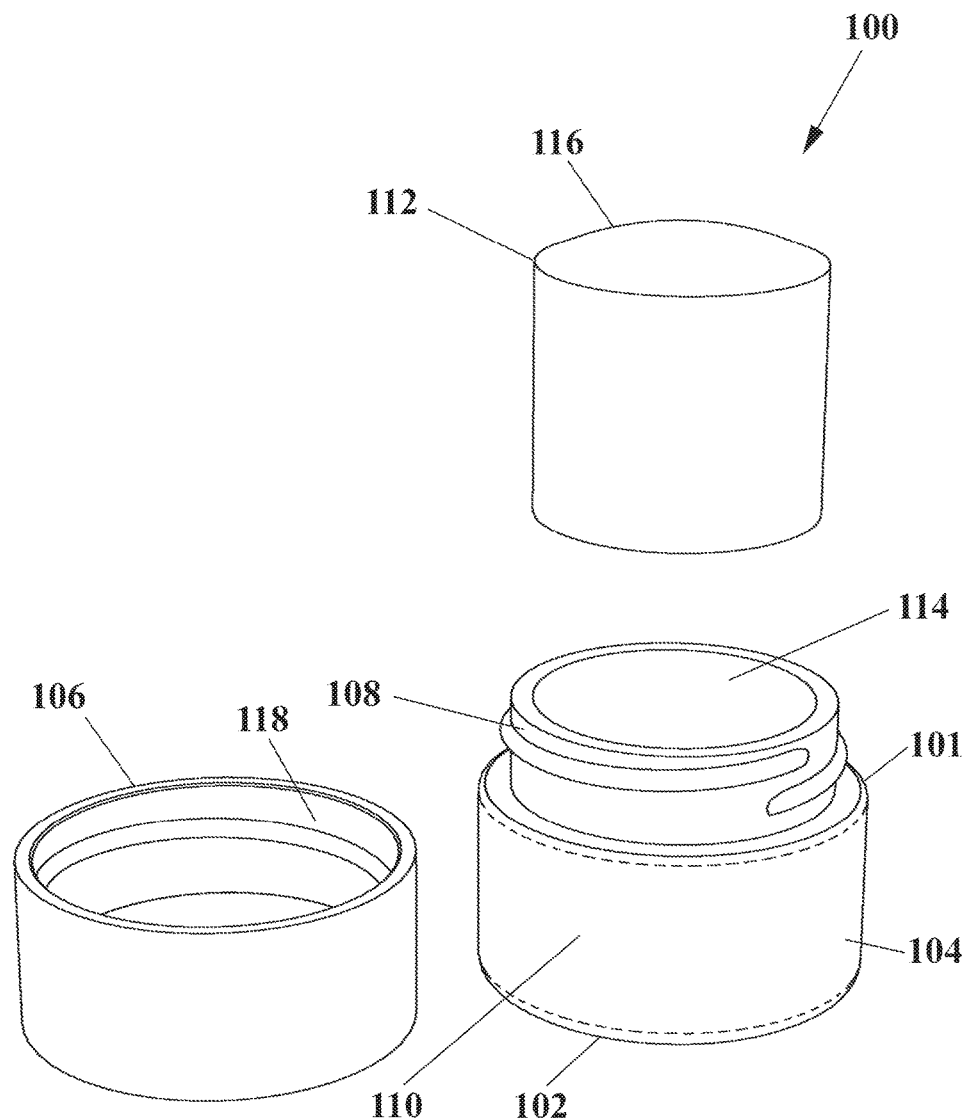

FIGS. 1A, 1B and 1C show a dispensing device 100 according to various embodiments of the present invention. As shown in these figures, the dispensing device 100 comprises a container 101, a porous applicator 112 in the container 101, and a cap 106. FIG. 1A shows the cap 106 connected to the container 101; FIG. 1B shows the cap 106 unconnected from the container 101; and FIG. 1C shows the cap 106 unconnected from the container 101 and the porous applicator 112 removed from the container 101.

The liquid dermatological agent is placed in the container 101 with the porous applicator 112. In the illustrated embodiment, the container 101 is a cylindrical container, although in other embodiments other three dimensional structures could be used, such as a rectangular prism. The container 101 comprises a bottom surface 102 and an annular sidewall 104 extending upward therefrom, which collectively define a reservoir 110 in which the liquid and porous applicator 112 are placed. The cap 106 preferably is detachably removable from an upper lip 108 of the sidewall 104 of the container 101. For example, the cap 106 could snap-fit to the upper lip 108 or, as shown in FIG. 1B, the cap 106 and upper lip 108 may comprise mating threaded portions so that cap 106 can be removably threaded to the container 101 through rotation of the cap 106 relative to the container 101 and upper lip 108.

The porous applicator 112 may be any suitable porous material that wicks the liquid dermatological agent in the container 101 through capillary action from the container 101 to a top surface 116 of the porous applicator 112 so that the liquid can be applied to a desired skin region of a user of the dispensing device 100. In various embodiments, the porous applicator 112 may comprise POREX® porous plastics, porous polymer fibers, and/or porous foam. POREX® is a trademark of Porex Corporation. The porous plastics can comprise various polymers including ultra-high molecular weight polyethylene (UHMWPE), high-density polyethylene (HDPE), polypropylene (PP), polytetrafluoroethylene (PTFE), polyvinylidene fluoride (PVDF), ethylene vinyl acetate (EVA), polyethersulfone (PES), polyurethane (PU) and/or PE/PP co-polymer as base materials. The porous polymer fibers can comprise polyester core fiber (PE/PET) fiber or bicomponent polyester sheath and polyester core fiber (PET/PET fiber). A synthetic fiber binding process can be used to extrude various profile polymer fiber geometries with various density, permeability, and wicking performance requirements. In addition, other polymer fibers such as polyolefins, nylon, cellulosic, acetate and other fibers may be blended and bonded together with PE/PET or PET/PET fiber. The porous foam can be polyurethane foam manufactured through a hydrophilic or hydrophobic polyurethane process. Such porous materials comprise pores with interconnected cavities such that fluidic communication throughout each porous material is enabled, thereby enabling the liquid in the container 101 to be delivered to the top surface 116 of the porous applicator 112. For example, porous polymer fibers are utilized to produce wicking media with open-cell pore structures that control liquid volume capacity and liquid transfer rates. The size of the pores of the porous materials varies depending on the material used. For example, the pore size diameters range from: 7 to 150 micrometers (mm) and up to 300 mm for PE, 80 to 150 mm for PP, 2 to 100 mm for polymer fibers, and 90 to greater than 350 mm for porous foam.

As mentioned above, the annular sidewall 104 may define a reservoir 110 containing the liquid. The liquid can be a dermatological agent, such as a cleansing agent, serum, cream, astringent, topical corticosteroid, emollient, exfoliator, skin treatment, or other suitable dermatological agent. For example, the dermatological agent can be a skin moisturizing cream or a skin pharmaceutical. The reservoir 110 may be coextensive with the internal volume of container 101. The annular sidewall 104 can also comprise an upper lip 108 that extends upward to define an upper opening for the container 101. In various embodiments, such as the embodiment shown in FIGS. 1A-1C, the upper opening is the only opening to the container 101. The cap 106 can comprise a correspondingly downward facing inner sidewall 118 configured to engage the upper lip 108 of the container 101 in a friction fit or threaded engagement, according to various embodiments. In this way, the cap 106 is attachable and detachable from the container 101. When the cap 106 is detachably removed from the container 101, the porous applicator 112 becomes visible and accessible to a user so that the liquid dermatological agent in the container 101 can be applied to the desired skin area via the top surface 116 of the porous applicator 112.

Preferably, the porous applicator 112 is positioned within the reservoir 110 and substantially fills the reservoir 110 such that the liquid in the container 101 is prevented from free-flowing out of the reservoir 110. Thus, the liquid may be dispensed from the dispensing device 100 without leaking. Prevention of liquid free flow is achieved based on the porous applicator 112 substantially filling the space defined by the reservoir 110 and a top surface 116 of the porous applicator 112 substantially filling the upper opening 114 of the container 101. This positioning of the porous applicator 112 in the container 101 creates a vacuum by absorption of the liquid by the pores of the porous applicator 112 that prevents the liquid from leaking out of the reservoir 110. As liquid absorption occurs by the porous applicator 112, the volume of the pores of the porous applicator increase, resulting in a corresponding decrease of the pressure within the pores according to Boyle's Law. Thus, the pores located at the topmost portion of the porous pad 112 have a lower pressure than the pressure of the air molecules at the top of the porous applicator 112. This results in a net inward force at the top surface 116 of the porous applicator 112 at the opening 114, which reduce or prevents leakage or spilling as liquid from the container 101 is dispensed via the porous applicator 112. In other words, liquid absorption of the pores creates a vacuum within the container 101. The vacuum slows the capillary flow of the liquid upwards and reduces or prevents leaking.

As shown in FIG. 1C, the shape of the porous applicator 112 preferably conforms to the internal volume of the container 101 such that the porous applicator 112 substantially fills the entire space defined by the reservoir 110 (i.e., fills the reservoir 110 enough to prevent leakage). Hence, in the embodiment shown in FIG. 1C, the porous applicator 112 is cylindrically shaped to match the shape of the container's reservoir 110. Thus, the porous applicator 112 fits snugly into the container 101. This can be advantageous because the porous applicator 112 can be easily inserted into the container 101 and remain in the inserted position without undesirable movement.

A user may comfortably access the liquid within the dispensing device 100 at the top surface 116 of the porous applicator 112 without external dripping or spilling of the liquid. As shown in FIG. 1C, the top surface 116 can have a convex curvature for direct application of the liquid by the user. In other embodiments, the top surface 116 could be flat or concave or some other desired profile. In other embodiments, the container 101 may comprise multiple compartments, with the porous applicator 112 and first liquid in one (or more) of the compartments. Another liquid dermatological agent (e.g., a cream) could be in another compartment, without the porous applicator, so that it is applied without a porous applicator.

Figure 2:
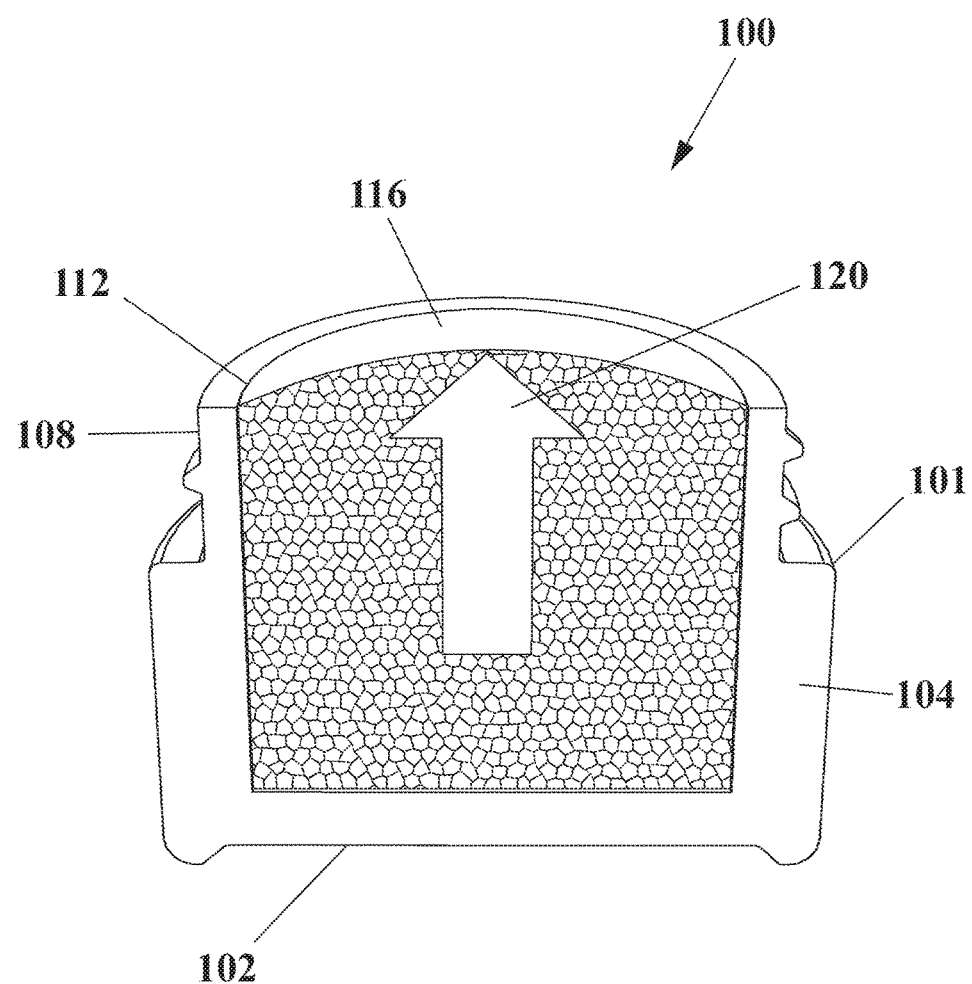

FIG. 2 is a cross section view of the dispensing device 100 according to various embodiments of the present invention. The cross section view illustrates the capillary action of the porous applicator 112. In various embodiments, a suitable molding process such as injection molding is used to mold the porous applicator 112 such that the porous applicator 112 comprises a plurality of open celled pores of varying sizes. In one embodiment, the varying size pores form a gradient such that the pore sizes are largest at the bottom of the porous applicator 112 and gradually decrease in size to the smallest pore sizes at the top surface 116 of the porous applicator 112. Accordingly, the liquid in the container 101 wicks upwards from the larger pores to the small pores, as denoted by the arrow 120. The pore size gradient contributes to the creation of the vacuum within the container 101. Specifically, larger pores absorb a relatively greater volume of liquid than absorbed by smaller pores. Consequently, when temperature is constant, according to Boyle's Law, the larger pores experience a corresponding relatively larger decrease in pressure than the smaller pores. Because the smaller pores have a relatively higher pressure than the larger pores, there is a corresponding force applied from the top surface 116 towards the bottom of the dispensing device 100, according to the progressively decreasing size of the pores from bottom to the top. This force resists the capillary action of the liquid, causing the capillary flow of the liquid to slow down. Leakage of the liquid out of the dispensing device 100 is prevented or reduced based on this inward force applied at the surface of the single opening 114.

The capillary action may be continuous such that the liquid continuously wicks upward to the pad 116 when there are pores available to absorb the liquid. Specifically, as a user dispenses the liquid by contacting the top surface 116 or the porous applicator, liquid is removed from the porous applicator, which is replenished based on the capillary action moving additional liquid to the top surface 116 of the porous applicator 112. Because the user contact for dispensing liquid removes liquid from the pores at the top surface 116, the volume increase caused by absorption is reversed and the volume of such top surface 116 pores decreases. As a result, pressure of the top surface pores increases, and the vacuum within the container 101 is temporarily released. When the top surface pores are replenished based on the continuous capillary action, the smaller top surface pores again absorb a relatively lesser volume of liquid and consequently have a greater pressure than the larger pores below the top surface 116. Thus, the vacuum is recreated as discussed above. The cycle of vacuum creation and release may advantageously enable continuous priming or supplying liquid to the pad 116 for dispensing liquid to the user, without leaks or spilling.

In addition, the porosity or wicking ability of the porous applicator 112 can be selected based on the liquid in the first container, since low viscosity liquids wick more easily than high viscosity liquids. Where the liquid is sufficiently viscous that the porous applicator can wick it continuously without additional external force, the container 101 could be made of a hard, rigid material, such as hard, rigid plastic, such as injection-molded or extruded high-density polyethylene (HDPE), which may be opaque or transparent. Where, however, the liquid is too viscous for the porous applicator alone to wick it without external forces, the container 101 could be made of a flexible, pliable material, such as a flexible, pliable plastic, so that the user could squeeze the container 101 to help force the liquid to the top surface 116 of the porous applicator 112. In this way, the combination of the capillary action from the porous applicator and an external force applied to the pliable container 101 by the user can enable the liquid to move to the top surface 116. Moreover, where the container 101 is made of pliable material, the porous applicator 112 can comprise a hydrophilic material for encouraging capillary flow of the porous applicator 112.

Figure 3:
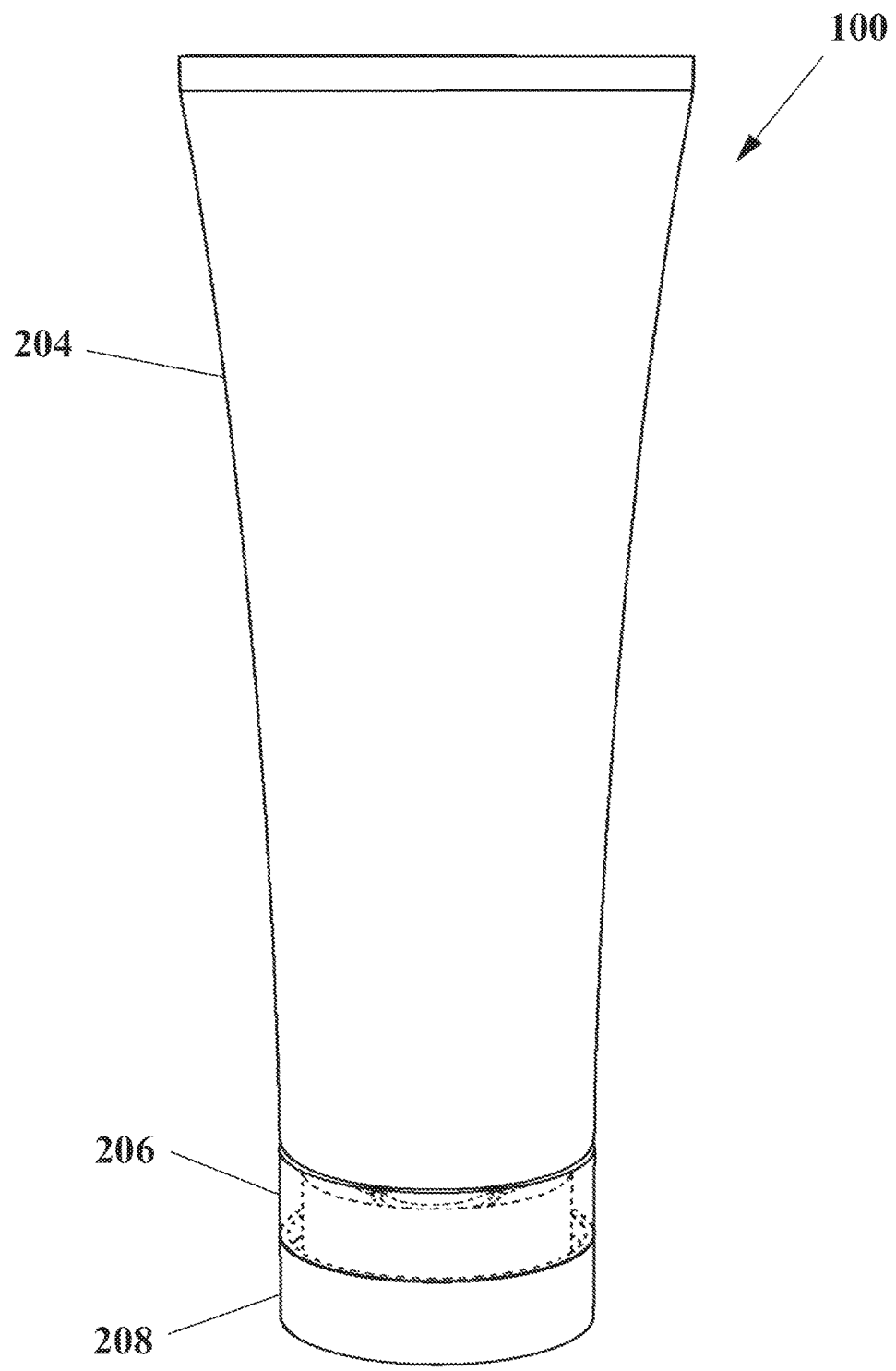
Figure 4:
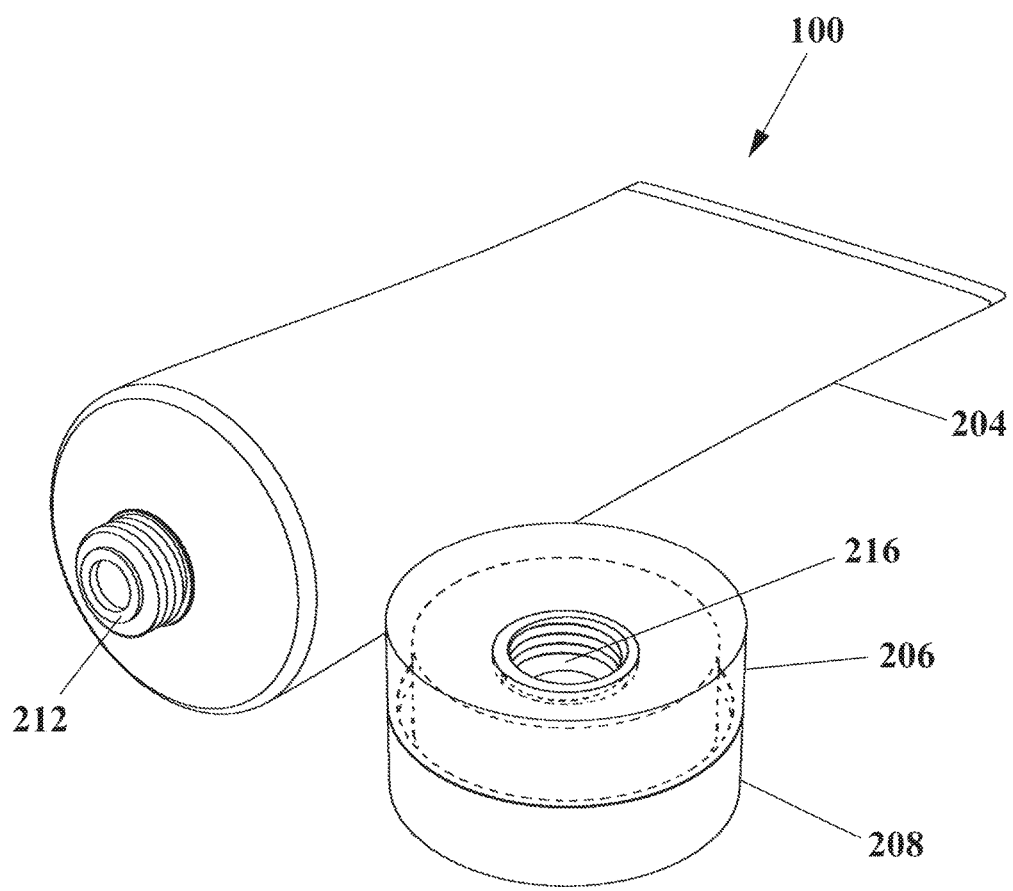

FIGS. 3 and 4 show a dispensing device 100 according to other embodiments of the present invention. In particular, the embodiments shown in FIGS. 3 and 4 include two containers 206, 204; hence it is a "dual container" dispensing device. The first container 206 can comprise and dispense (via the porous applicator 112) a first liquid dermatological agent and the second container can comprise and dispense a second dermatological agent that is the same as or, preferably, different from the first dermatological agent. The first container 206 is similar to the container 101 in FIGS. 1A-1C, but in the dual container configuration can also serve as a cap for the second container 204. The second container 204 can comprise a squeeze tube, for example. In that connection, the first container 206 may comprise a circular post which extends into the interior reservoir defined by the first container 206. The circular post may define a threaded recess 216 for receiving a corresponding threaded post 212 of the second container 204. The first container 206, therefore, can be removably attachable to the second container 204 by screwing the threaded post 212 of the second container 204 into the threaded recess 216 of the first container 206 (i.e. fully attached when fully threaded) and detachable by unscrewing the threaded post 212 from the threaded recess 216 (i.e. fully detached when fully unthreaded). The threaded recess 216 can comprise a top surface or cover that prevents the liquid from the second container 204 from flowing into the first container 206 when the first and second containers 206, 204 are coupled together in this manner. FIG. 3 show the first and second containers 206, 204 attached together while FIG. 4 shows the first and second containers 206, 204 detached separately (with the first container 206 upside down).

The first container 206 also comprises the porous applicator 112 and the dispensing device 100 can additionally comprise an overcap 208 that is similar to the cap 106 in the embodiments of FIGS. 1A-1C. The overcap 208 may be attached or coupled to the first container 206 via a suitable attachment means, as described above.

The first container 206 is preferably made of a hard, rigid, non-pliable material, such as a hard, rigid plastic, such as injection-molded or extruded high-density polyethylene (HDPE), which may be opaque or transparent; and the second container 204 is preferably made from a pliable material, such as a pliable plastic, such as injection-molded or extruded low-density polyethylene (LDPE).

Figure 5A:
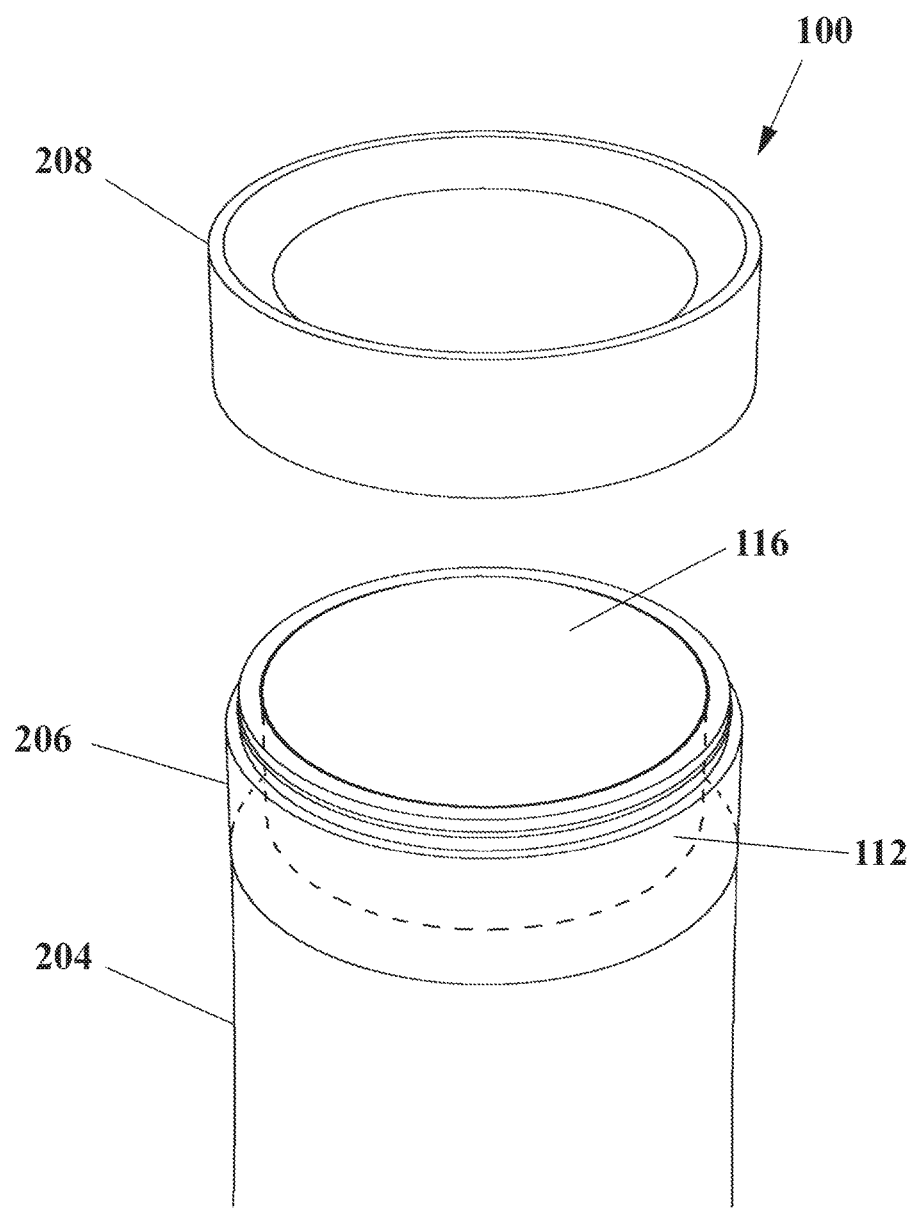
Figure 5B:
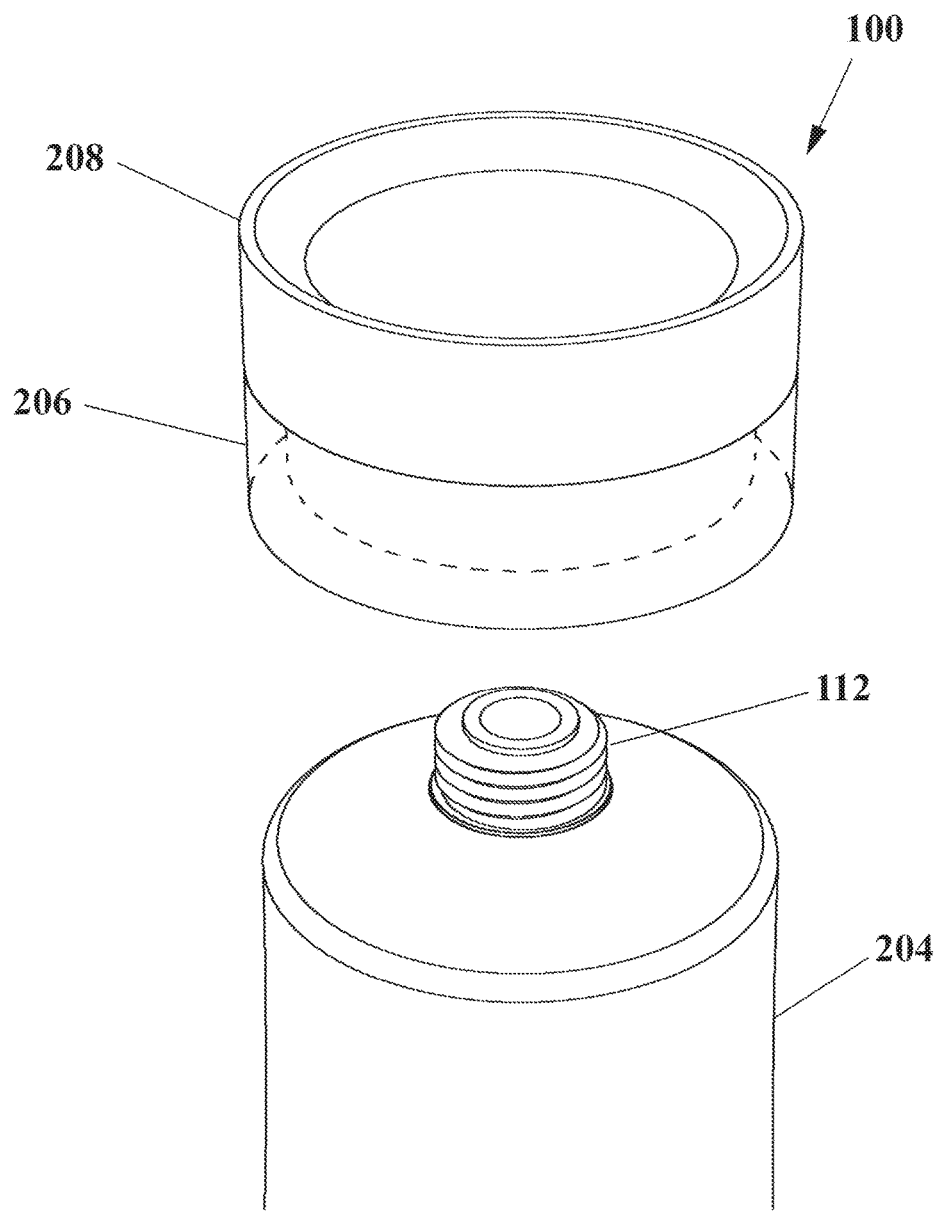

FIGS. 5A-5B are views of the dual configuration dispensing device 100 with components of the first container 206 detached from the second container 204 according to various embodiments of the present invention. FIG. 5A illustrates that the overcap 208 removed for application of the first liquid using the porous applicator 112. In one embodiment, the user may simply twist off the overcap 208 to detach it from the first container 206. Twisting off the overcap 208 enables the user to directly apply the first liquid using the porous applicator 112 with the advantage of reduction or prevention of leakage as discussed above. The porous applicator 112 is saturated such that the open celled pores of the porous applicator 112 absorb the first liquid in the first container 206, as described above.

The user may also twist off the entire first container 206 by unscrewing the threaded post 212 of the second container 204 from the threaded recess 216 of the first container 206.

With the first and second containers 206, 204 detached, the user may apply a force to the second container 204 (e.g., squeeze it) to dispense the second liquid from an opening in the threaded post 212. Accordingly, there can be at least two different methods of dispensing the two liquids from the dispensing device 100, with at least one method for each of the two liquids, respectively.

Figure 6:
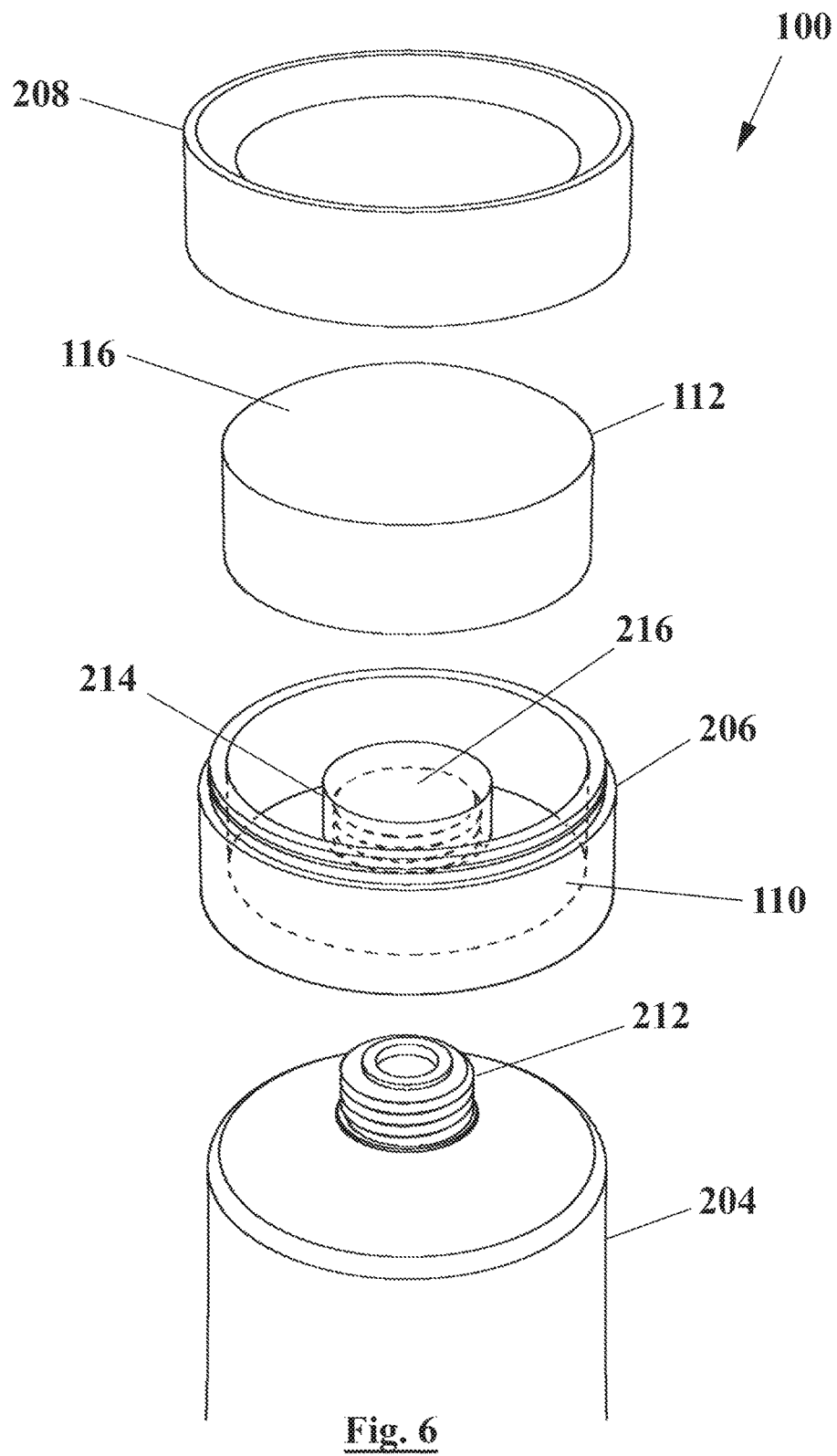

FIG. 6 is an exploded view of the dispensing device 100 positioned with the components of the first container 206 on top of the second container 204 according to various embodiments of the present invention. As shown in FIG. 6, the first container 206 may have a circular, internally-threaded post 214 that extend from the bottom surface of the first container 206 into the reservoir 110 defined by the first container 206. In various embodiments, the circular post 214 can comprise a downward-facing threaded recess 216 for receiving the corresponding threaded post 212 of the second container 204 for attachment and detachment of the first and second containers 206, 204. Although the circular post 214 of the first container 206 and the threaded post 212 of the second container 204 are both circular shaped, other suitable shapes are also possible. The porous applicator 112 may be shaped and sized to fit snugly into the reservoir 110 of the first container 206 so that the first liquid in the reservoir 110 can be wicked to the top surface 116 of the porous applicator 112 with reduced or prevented leakage of the first liquid from the first container 206. To that end, at least part of the porous applicator 112 may be hollow to accommodate the post 214 extending there into. Also, the post 214 may have top surface or cover at the top end of the recess to prevent the second liquid, in the second container 204, from being dispensed into the first container 206 when the two are connected.

Figure 7A:
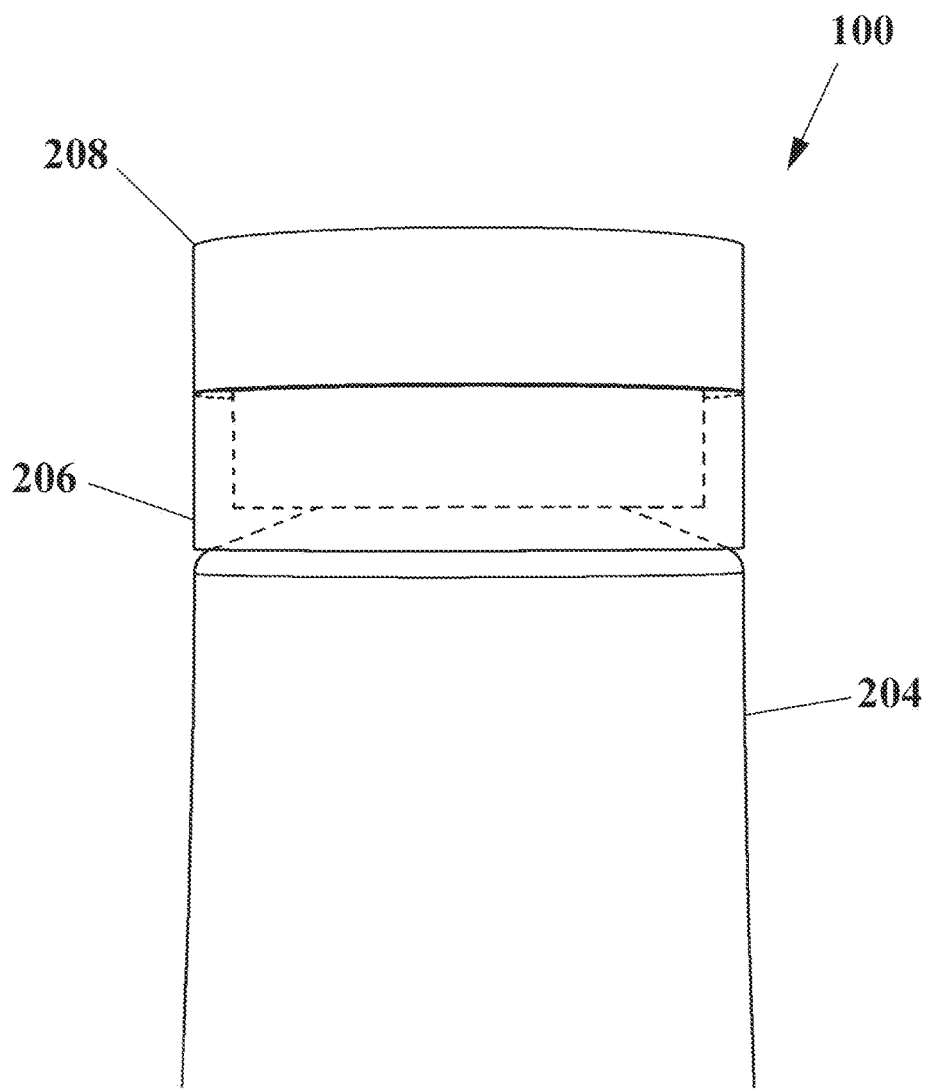
Figure 7B:
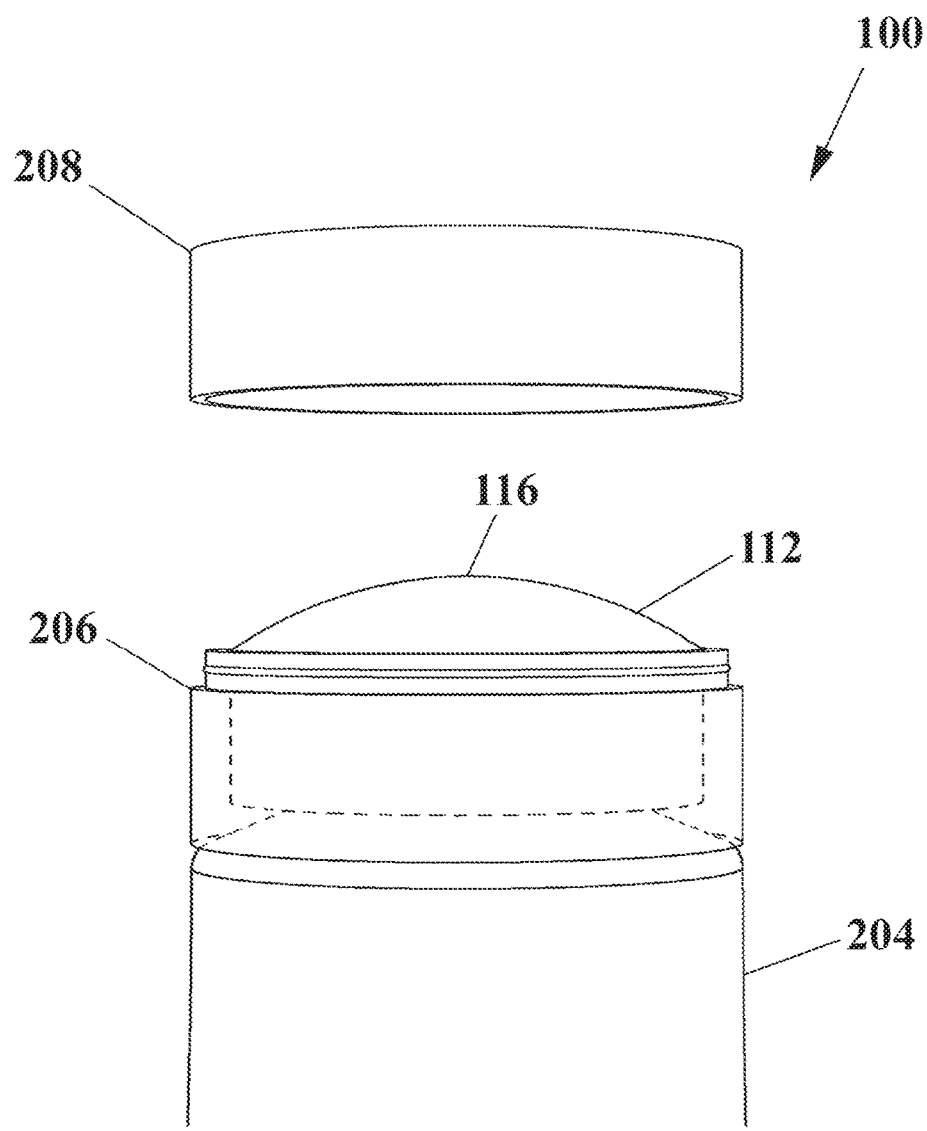
Figure 7C:
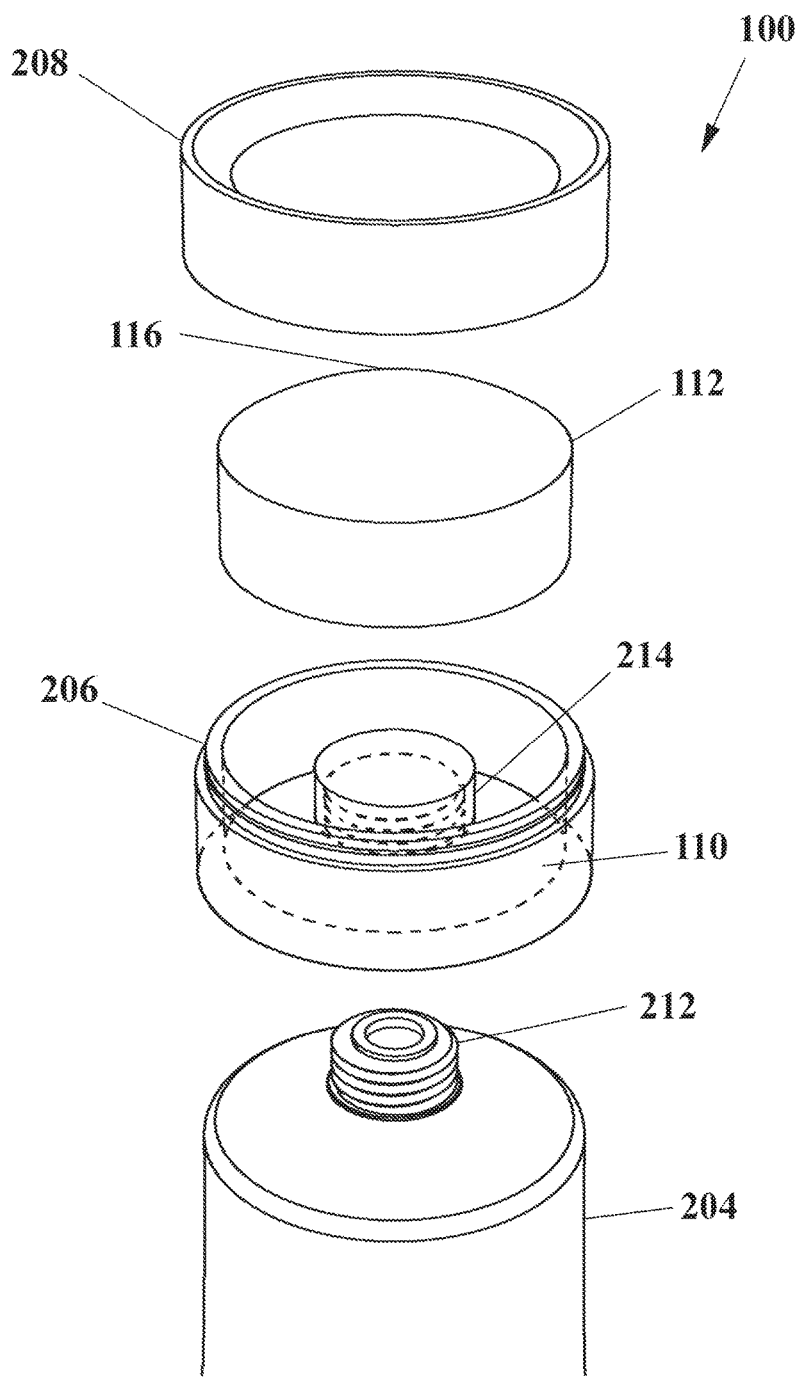

FIGS. 7A, 7B, 7C show additional views of the dual container dispensing device 100 according to various embodiments of the present invention. FIG. 7A shows the overcap 208 attached to the first container 206, with the first container 206 secured (threaded) to the second container 204. FIG. 7B shows the overcap 208 removed. And FIG. 7C is an exploded view showing the cap 208 detached, the porous applicator 112 out of the first container 206, and the first container 206 unthreaded from the second container 204.

Figure 8A:
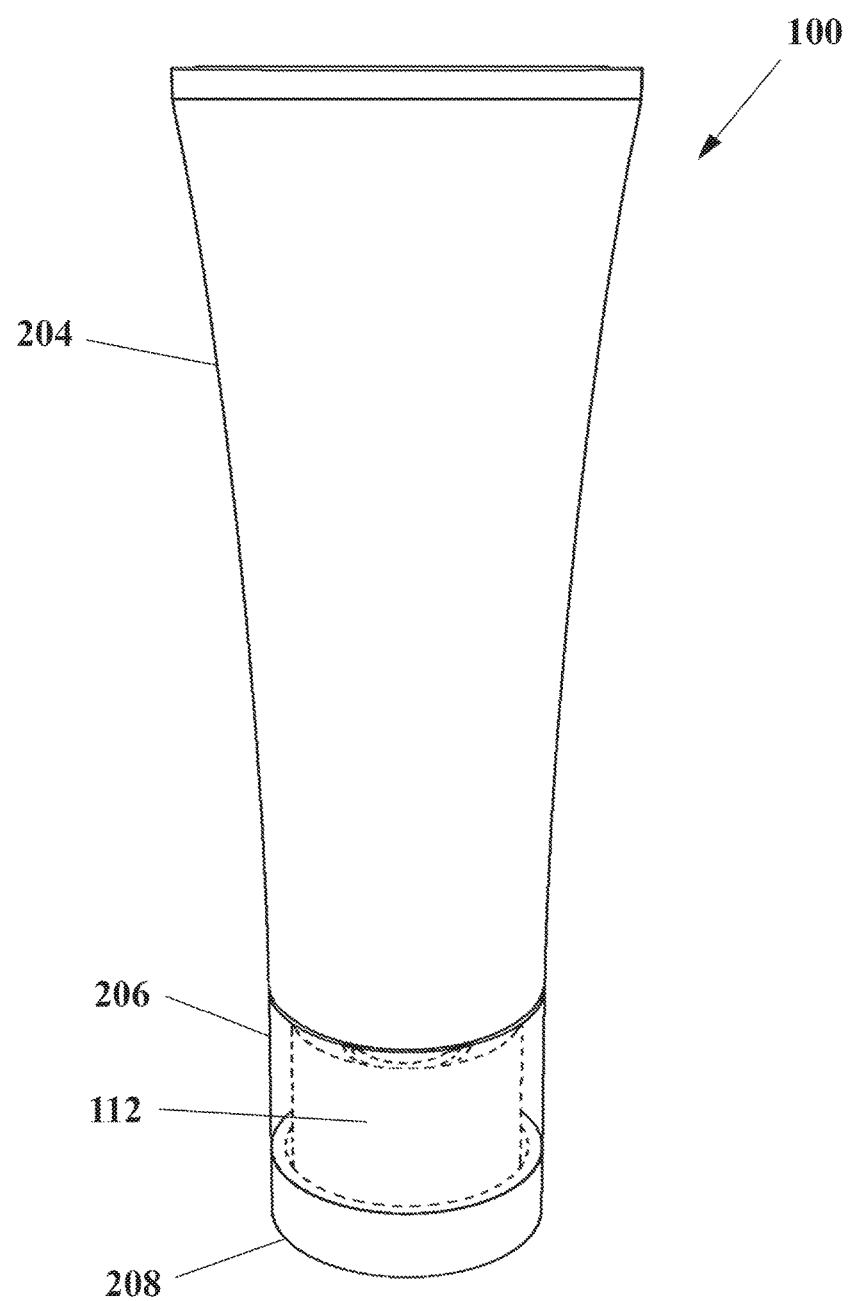
Figure 8B:
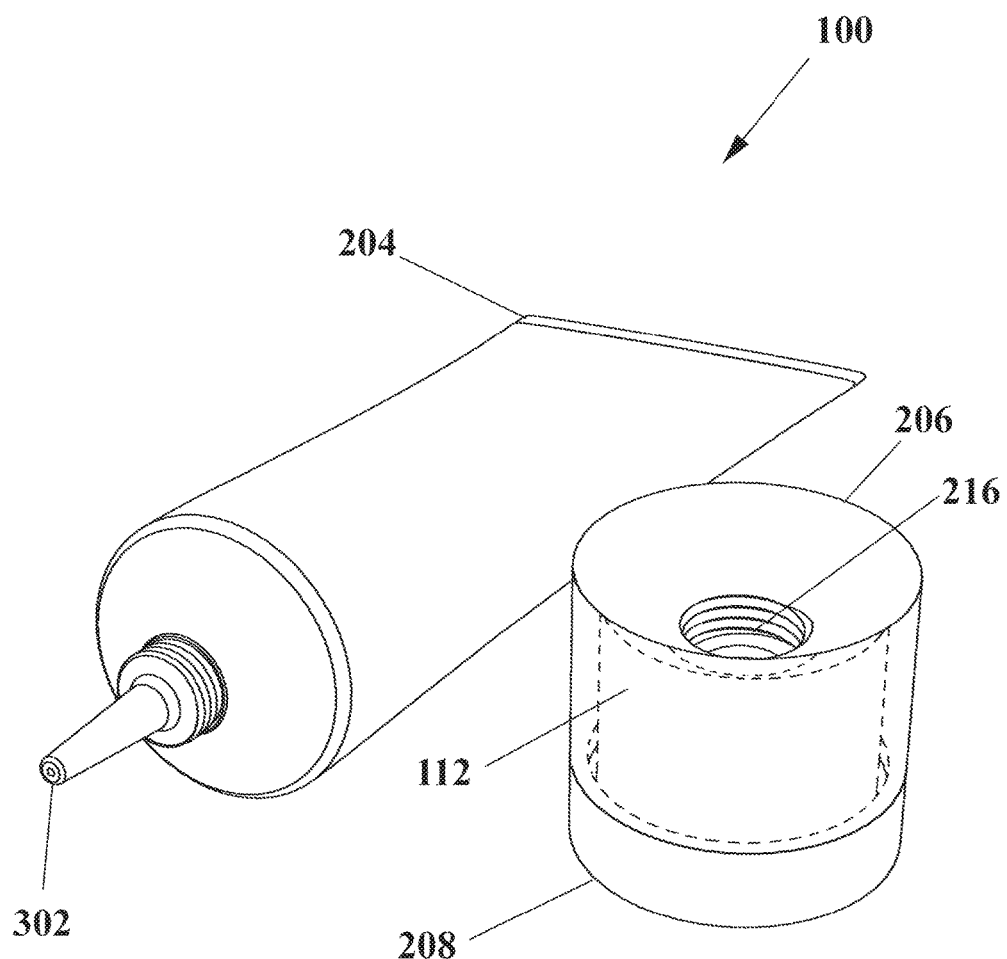
Figure 9A:
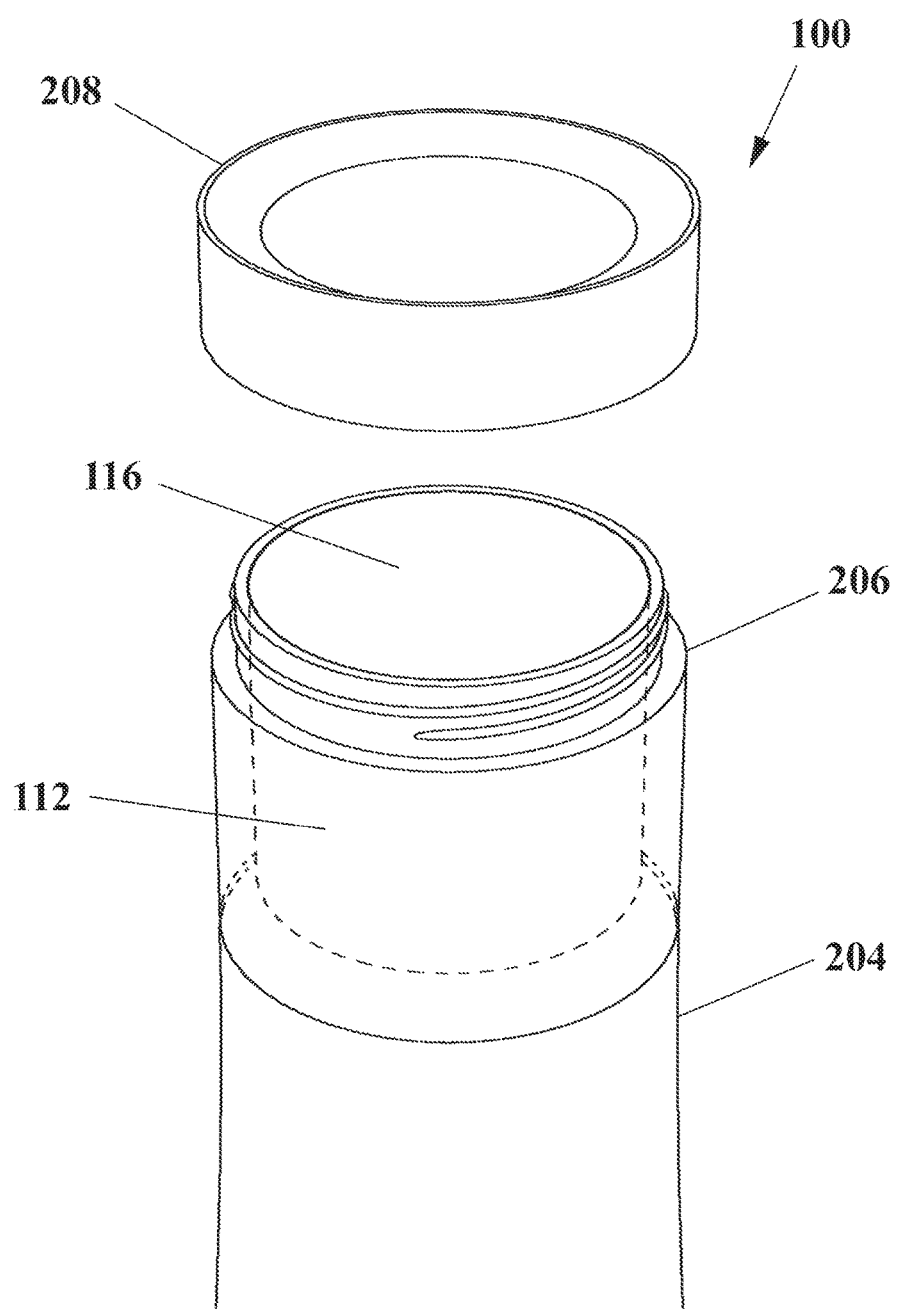
Figure 9B:
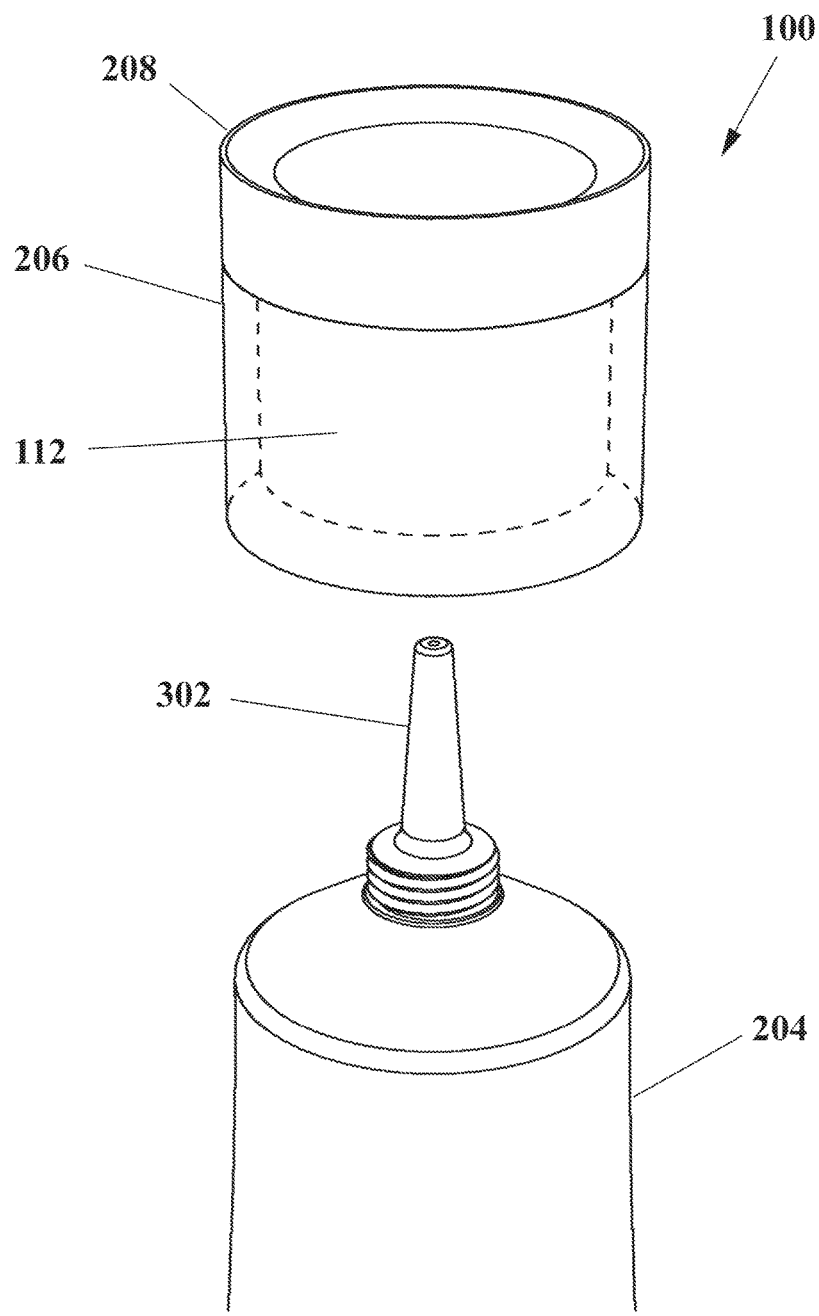
Figure 10A:
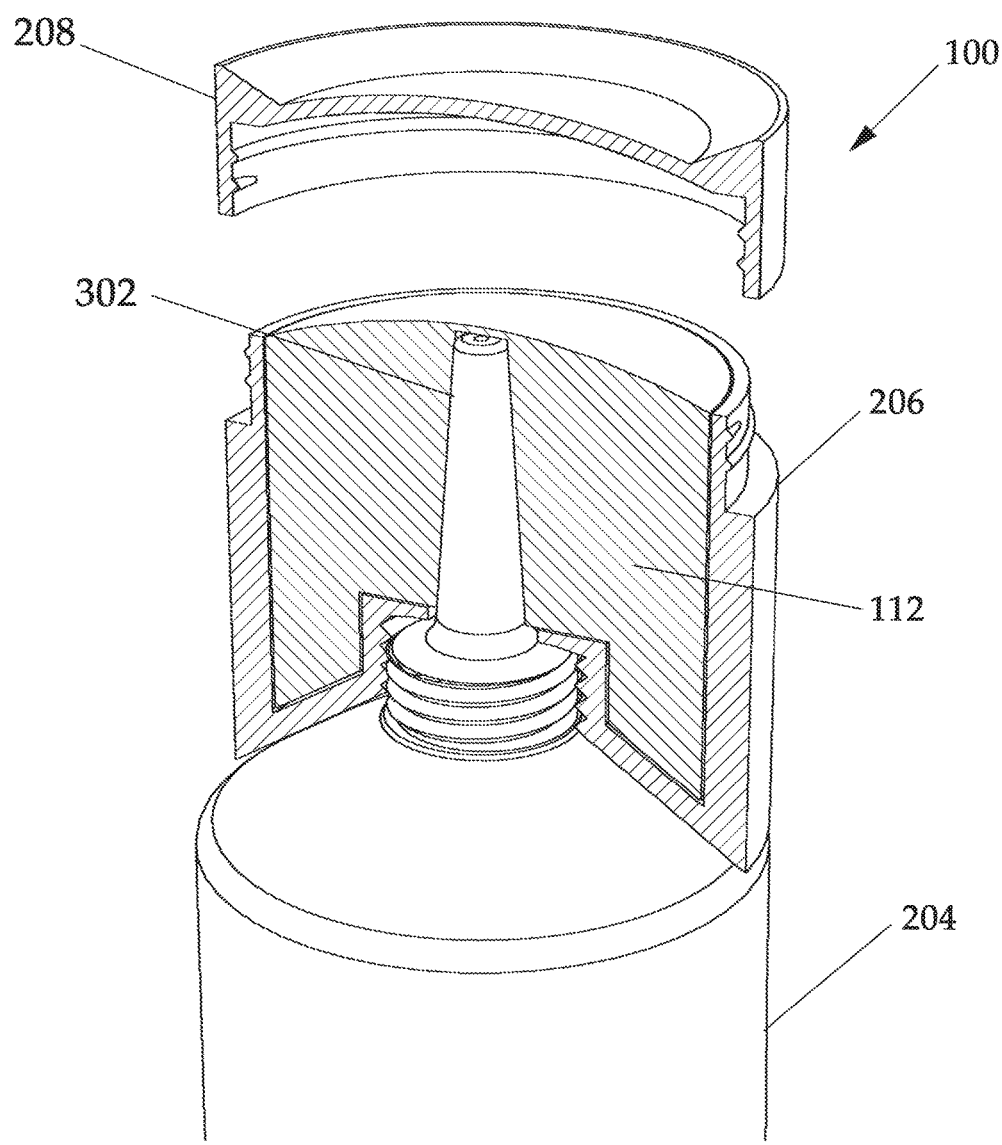
Figure 10B:
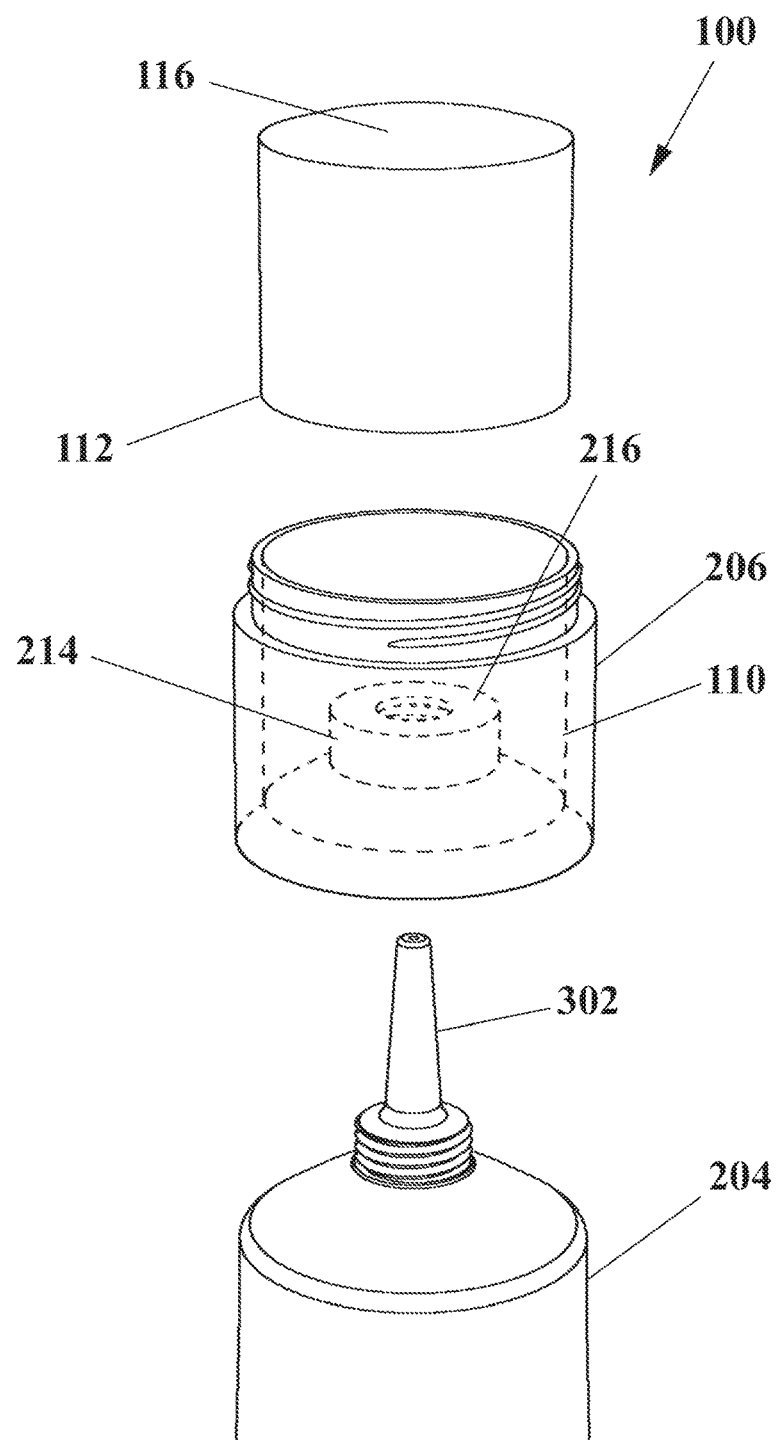

In other embodiments, as shown in FIGS. 8A-8B, the threaded post 212 of the second container 204 comprises an integrally-formed, elongated applicator tip 302. The applicator tip 302 can extend into and through the threaded recess 216 of the circular post 214. As such, in such an embodiment, the circular post 214 of the first container 206 does not include the top cover, thereby allowing the top of the tip 302 to pass through the circular post 214 into the porous applicator 112. Because the applicator tip 302 is elongated, the first container 206 and the porous applicator 112 can be correspondingly elongated. The applicator tip 302 could be useful for ophthalmic purposes or other suitable dispensing purposes. For example, the liquid dispensed by the first and/or second containers could be eye makeup remover.

FIGS. 9A-9B and 10A-10B are views of the dual configuration dispensing device 100 with the extended tip for the second (e.g., squeeze tube) container 204 according to various embodiments of the present invention. In this illustrated embodiment, the upper end of the tip does not reach the top surface 116 of the porous applicator 112 when the second container 204 is fully treaded to the first container. In use, therefore, the user can squeeze the second container to dispense the second liquid into the porous applicator 112, such that porous applicator 112 comprises both the first and second liquids, so that the user could simultaneously apply both liquids with the porous applicator 112. In this manner, the first and second liquids may be mixed together before dispensing via the porous applicator 112 to the desired area of application. For example, the second liquid could comprise a skin color or pigment agent that could be mixed with the first liquid to dispense a colored or pigmented first liquid. The user can apply just the first liquid by not squeezing the second container 204, and thereby not dispensing the second liquid into the porous applicator 112, although residual amounts of the second liquid could still be in the porous applicator 112 from a prior dispensing of the second liquid into the porous applicator. And the user could apply the second liquid, without the first liquid, by removing the first container 206 from the second container 204 and applying the second liquid via the tip 302 to the desired area with the first container 206 removed.

In other embodiments, as shown in FIGS. 11 and 12, the tip 302 could extend through to the top of the porous applicator 112. As such, the top surface of the porous applicator 112 can comprise an opening to which the tip 302 from the second container 204 extends. As such, the user can simultaneously apply the first and second liquids, but without mixing them prior to application, by simultaneously squeezing the second container 204, such that the second liquid is dispensed through the tip 302, and applying the first liquid with the porous applicator 112. FIG. 12 shows a cross section view of the porous applicator 112 and the overcap 208 according to various embodiments of the present invention. This figure shows that the overcap 208 can comprises a downward facing pintle 250 for plugging the opening in the tip 302 of the second container 204 when the first and second containers are connected and the overcap 208 is connected to the first container 206.

In one general aspect, therefore, the present invention is directed to a dispensing device that comprises a first container 101, 206 having a sidewall 104 that defines a reservoir 110. The first container has an upper opening to the reservoir at a top of the first container. And there is a first liquid in the reservoir, where the first liquid comprises a dermatological agent. A porous applicator 112 is in the reservoir. The porous applicator comprises open-celled pores that extend from a bottom of the porous applicator to a top surface of the porous applicator, such that the open-celled pores are filled with the first liquid such that the pores deliver the first liquid to the top surface of the porous applicator by capillary action, and such that the porous applicator substantially fills the reservoir and the upper opening at the top of the first container such that the first liquid is prevented from free-flowing out of the reservoir.

In various implementations, the upper opening of the first container is the only opening of the first container. And the porous applicator delivers the first liquid to the top surface of the porous applicator without use of a pump or buffer.

In other various implementations, the sidewall of the first container comprises an upper lip (or neck portion), and the dispensing device further comprises a cap 106, 208 that comprises a downward facing sidewall for engaging the upper lip (or neck portion) of the first container such that the cap is detachably removable from the first container to reveal the porous applicator.

In still other implementations, the dispensing device comprises a second container 204, e.g., a squeeze tube, containing a second liquid. The second liquid may comprise a second dermatological agent that is different from the first liquid; the second container may have a circular, threaded post 212 at an upper end of the second container; the first container comprises a circular post 214 that extends upward from a lower, central portion of the first container into the reservoir; the circular post of the first container comprises a downward-facing threaded recess 216 for receiving the threaded post of the second container such that first container is detachably removable from the second container by unscrewing the first container. The first container may comprise a hard, rigid plastic and the second container may comprise a pliable plastic.

In various implementations, the circular post of the first container comprises an upper wall that blocks the second liquid from entering the reservoir defined by the first container. In other embodiments, the threaded post of the second container comprises a tip that extends from the threaded post of the second container into the porous applicator when the first container is attached to the second container. In such embodiments, the tip can comprise an opening for dispensing the second liquid that is in the second container. The upper (or distal) end of the tip can terminate below or at the top surface of the porous applicator when the threaded post of the second container is fully threaded into the circular post of the first container. Also, the cap can comprise a downward facing pintle that is inserted into the opening of the tip of the second container when the cap is attached to the first container the threaded post of the second container is fully threaded into the circular post of the first container.

The dermatological agents of the first and second liquids can be cosmetic or pharmaceutical dermatological agents, such as cosmetic or pharmaceutical creams, oils, lotions, etc.

Although various embodiments have been described herein, many modifications, variations, substitutions, changes, and equivalents to those embodiments may be implemented and will occur to those skilled in the art. For example, where example materials are disclosed for certain components, other materials may be used. It is therefore to be understood that the foregoing description and the appended claims are intended to cover all such modifications and variations as falling within the scope of the disclosed embodiments. The following claims are intended to cover all such modification and variations.

In summary, numerous benefits have been described which result from employing the inventions described herein. The foregoing description of the embodiments has been presented for purposes of illustration and description. It is not intended to be exhaustive or limiting to the precise form disclosed. Modifications or variations are possible in light of the above teachings. The one or more embodiments were chosen and described in order to illustrate principles and practical application to thereby enable one of ordinary skill in the art to utilize the various embodiments and with various modifications as are suited to the particular use contemplated. It is intended that the claims submitted herewith define the overall scope.

What is claimed is:

1. A dispensing device comprising:
    a first container having a sidewall that defines a reservoir, the first container having an upper opening to the reservoir at a top of the first container;
    a first liquid in the reservoir, wherein the first liquid comprises a dermatological agent; and
    a porous applicator in the reservoir, wherein the porous applicator comprises an injection-molded polyethylene body having open-celled pores, wherein the open-celled pores extend from a bottom of the porous applicator to a top surface of the porous applicator, wherein the open-celled pores are filled with the first liquid such that the pores deliver the first liquid to the top surface of the porous applicator by capillary action without externally-applied pressure, wherein the porous applicator substantially fills the reservoir and the upper opening at the top of the first container such that the first liquid is prevented from free-flowing out of the reservoir.

2. The dispensing device of claim 1, wherein the first container comprises a hard, rigid plastic.

3. The dispensing device of claim 1, wherein the upper opening is the only opening of the first container.

4. The dispensing device of claim 1, wherein:
    the sidewall of the first container comprises an upper lip; and
    the dispensing device further comprises a cap that comprises a downward facing sidewall for engaging the upper lip of the first container such that the cap is detachably removable from the first container to reveal the porous applicator.

5. The dispensing device of claim 1, further comprising a second container containing a second liquid, wherein:
    the second liquid comprises a second dermatological agent that is different from the first liquid;
    the second container has a circular, threaded post at an upper end of the second container;
    the first container comprises a circular post that extends upward from a lower, central portion of the first container into the reservoir; and
    the circular post of the first container comprises a downward-facing threaded recess for receiving the threaded post of the second container such that first container is detachably removable from the second container by unscrewing the first container.

6. The dispensing device of claim 5, wherein:
    the first container comprises a hard, rigid plastic; and
    the second container comprises a squeeze tube that comprises a pliable plastic.

7. The dispensing device of claim 6, wherein the circular post of the first container comprises an upper wall that blocks the second liquid from entering the reservoir defined by the first container.

8. The dispensing device of claim 6, wherein:
    the threaded post of the second container comprises a tip that extends from the threaded post of the second container into the porous applicator when the first container is attached to the second container; and
    the tip comprises an opening for dispensing the second liquid that is in the second container.

9. The dispensing device of claim 8, wherein an end of the tip is below the top surface of the porous applicator when the threaded post of the second container is fully threaded into the circular post of the first container.

10. The dispensing device of claim 8, wherein an end of the tip protrudes to the top surface the porous applicator when the threaded post of the second container is fully threaded into the circular post of the first container.

11. The dispensing device of claim 10, wherein the cap comprises a downward facing pintle that is inserted into the opening of the tip of the second container when:
    the cap is attached to the first container; and
    the threaded post of the second container is fully threaded into the circular post of the first container.

12. The dispensing device of claim 5, wherein the second liquid comprises a skin color or pigment liquid.

13. The dispensing device of claim 1, wherein:
the first container defines first and second reservoirs;
the first liquid and the porous applicator are in the first reservoir; and
a cream is in the second reservoir.

14. The dispensing device of claim 1, wherein the dermatological agent comprises a dermatological agent selected from the group comprising a skin moisturizing cream, skin cleanser, oil, and lotion.

15. The dispensing device of claim 1, wherein the dermatological agent comprises a skin pharmaceutical.

16. The dispensing device of claim 1, wherein the dermatological agent comprises an eye makeup remover.

17. A dispensing device comprising:
a first container having a sidewall that defines a reservoir, the first container having an upper opening to the reservoir at a top of the first container;
a first liquid in the reservoir, wherein the first liquid comprises a dermatological agent;
a porous applicator in the reservoir, wherein the porous applicator comprises open-celled pores that extend from a bottom of the porous applicator to a top surface of the porous applicator, wherein the open-celled pores are filled with the first liquid such that the pores deliver the first liquid to the top surface of the porous applicator by capillary action, wherein the porous applicator substantially fills the reservoir and the upper opening at the top of the first container such that the first liquid is prevented from free-flowing out of the reservoir;
a second container containing a second liquid, wherein:
the second liquid comprises a second dermatological agent that is different from the first liquid;
the second container has a circular, threaded post at an upper end of the second container;
the first container comprises a circular post that extends upward from a lower, central portion of the first container into the reservoir; and
the circular post of the first container comprises a downward-facing threaded recess for receiving the threaded post of the second container such that first container is detachably removable from the second container by unscrewing the first container.

18. The dispensing device of claim 17, wherein the porous applicator delivers the first liquid to the top surface of the porous applicator without externally-applied pressure.

19. The dispensing device of claim 17, wherein the porous applicator comprises a porous plastic material.

20. The dispensing device of claim 17, wherein the porous applicator comprises a porous polymer fiber.

21. The dispensing device of claim 17, wherein the porous applicator comprises a porous foam.

* * * * *